US009173766B2

(12) United States Patent
Sung et al.

(10) Patent No.: US 9,173,766 B2
(45) Date of Patent: Nov. 3, 2015

(54) SYSTEMS AND METHODS TO TREAT UPPER PHARYNGEAL AIRWAY OF OBSTRUCTIVE SLEEP APNEA PATIENTS

(75) Inventors: An-Min Jason Sung, Warren, NJ (US); Robert A. Rousseau, Ottsville, PA (US); David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 586 days.

(21) Appl. No.: 13/486,293

(22) Filed: Jun. 1, 2012

(65) Prior Publication Data

US 2013/0319427 A1 Dec. 5, 2013

(51) Int. Cl.
*A61F 5/56* (2006.01)

(52) U.S. Cl.
CPC .................................... *A61F 5/566* (2013.01)

(58) Field of Classification Search
USPC .......... 128/848, 859–862; 433/6–7; 602/902; 600/228; 623/11.11
See application file for complete search history.

(56) References Cited

U.S. PATENT DOCUMENTS 2,705,492 A 4/1955 Chandler
3,123,007 A 3/1964 Orr
3,378,010 A 4/1968 Codling et al.
4,024,855 A 5/1977 Bucalo
4,069,865 A 1/1978 Gazda et al.
4,290,763 A 9/1981 Hurst
4,523,584 A 6/1985 Lynch
4,557,264 A 12/1985 Hinsch
4,839,215 A 6/1989 Starling et al.
4,881,939 A 11/1989 Newman
4,950,285 A 8/1990 Wilk et al.
5,053,047 A 10/1991 Yoon
5,067,485 A 11/1991 Cowen
5,123,913 A 6/1992 Wilk et al.
5,192,271 A 3/1993 Kalb et al.
5,192,274 A 3/1993 Bierman
5,269,783 A 12/1993 Sander
5,284,161 A 2/1994 Karell
5,311,028 A 5/1994 Glavish
5,393,984 A 2/1995 Glavish
5,483,077 A 1/1996 Glavish
5,484,444 A 1/1996 Braunschweiler et al.
5,485,444 A 1/1996 Kühn et al.
5,609,559 A 3/1997 Weitzner
5,683,417 A 11/1997 Cooper
5,704,895 A 1/1998 Scott et al.
5,792,067 A 8/1998 Karell
5,843,077 A 12/1998 Edwards (Continued)

FOREIGN PATENT DOCUMENTS

CN 2465680 12/2001
CN 201029957 3/2008

(Continued)

OTHER PUBLICATIONS

U.S. Appl. No. 13/486,293 filed Jun. 1, 2012.

(Continued)

*Primary Examiner* — Ophelia A Hawthorne

(57) ABSTRACT

Obstructive Sleep Apnea (OSA) may be caused by a collapse of the pharyngeal wall as a result of increasing negative airway pressure. This invention is directed to systems and methods to resist collapse of the pharyngeal wall by minimally invasive upper pharyngeal airway surgery.

10 Claims, 5 Drawing Sheets

(56) References Cited

U.S. PATENT DOCUMENTS 5,931,855 A 8/1999 Buncke
6,161,541 A 12/2000 Woodson
6,190,401 B1 2/2001 Green et al.
6,241,747 B1 6/2001 Ruff et al.
6,250,307 B1 6/2001 Conrad et al.
6,348,156 B1 2/2002 Vishnoi et al.
6,408,851 B1 6/2002 Karell
6,431,174 B1 8/2002 Knudson et al.
6,457,472 B1 10/2002 Schwartz et al.
6,513,530 B2 2/2003 Knudson et al.
6,523,542 B2 2/2003 Knudson et al.
6,578,580 B2 6/2003 Conrad et al.
6,589,549 B2 7/2003 Shih et al.
6,599,310 B2 7/2003 Leung et al.
6,627,600 B2 9/2003 Boutignon
6,634,362 B2 10/2003 Conrad et al.
6,638,284 B1 10/2003 Rousseau et al.
6,716,251 B1 4/2004 Asius et al.
6,742,524 B2 6/2004 Knudson et al.
6,755,868 B2 6/2004 Rousseau
6,800,082 B2 10/2004 Rousseau
6,899,105 B2 5/2005 Krueger et al.
6,955,172 B2 10/2005 Nelson et al.
6,981,944 B2 1/2006 Jamiolkowski et al.
7,017,582 B2 3/2006 Metzger et al.
7,056,331 B2 6/2006 Kaplan et al.
7,135,189 B2 11/2006 Knapp
7,146,981 B2 12/2006 Knudson et al.
7,166,570 B2 1/2007 Hunter et al.
7,213,599 B2 5/2007 Conrad et al.
7,237,554 B2 7/2007 Conrad et al.
7,261,702 B1 8/2007 Alexandre et al.
7,288,075 B2 10/2007 Parihar et al.
7,297,102 B2 11/2007 Smith et al.
7,322,993 B2 1/2008 Metzger et al.
7,337,781 B2 3/2008 Vassallo
7,360,432 B2 4/2008 Lehtonen
7,360,542 B2 4/2008 Nelson et al.
7,367,340 B2 5/2008 Nelson et al.
7,401,611 B2 7/2008 Conrad et al.
7,442,389 B2 10/2008 Quelle et al.
7,601,164 B2 10/2009 Wu
7,669,603 B2 3/2010 Knudson et al.
7,806,908 B2 10/2010 Ruff
7,850,894 B2 12/2010 Lindh, Sr.
7,857,829 B2 * 12/2010 Kaplan et al. ................. 606/228
7,888,119 B2 2/2011 Sugaya et al.
8,142,422 B2 3/2012 Makower et al.
8,307,831 B2 11/2012 Rousseau
8,413,661 B2 4/2013 Rousseau et al.
8,800,567 B2 * 8/2014 Weadock et al. ............. 128/848
2001/0037133 A1 11/2001 Knudson et al.
2002/0144685 A1 10/2002 Ivanovich et al.
2003/0004579 A1 1/2003 Rousseau et al.
2003/0034312 A1 2/2003 Unger et al.
2003/0149445 A1 8/2003 Knudson et al.
2003/0149447 A1 8/2003 Morency et al.
2003/0149488 A1 8/2003 Metzger et al.
2003/0176875 A1 9/2003 Anderson et al.
2004/0020492 A1 2/2004 Dubrul et al.
2004/0020498 A1 2/2004 Knudson et al.
2004/0028676 A1 2/2004 Klein et al.
2004/0044366 A1 3/2004 Bonutti et al.
2004/0102796 A1 5/2004 Hill et al.
2004/0139975 A1 7/2004 Nelson et al.
2004/0144395 A1 7/2004 Evans et al.
2004/0147811 A1 7/2004 Diederich et al.
2004/0149290 A1 8/2004 Nelson et al.
2004/0153127 A1 8/2004 Gordon et al.
2004/0231678 A1 11/2004 Fierro
2005/0038472 A1 2/2005 Furst
2005/0082452 A1 4/2005 Kirby
2005/0092334 A1 5/2005 Conrad et al.
2005/0115572 A1 6/2005 Brooks et al.
2005/0121039 A1 6/2005 Brooks et al.
2005/0126563 A1 6/2005 van de Burg et al.
2005/0159637 A9 7/2005 Nelson et al.
2005/0165352 A1 7/2005 Henry et al.
2005/0199248 A1 9/2005 Pflueger et al.
2005/0203576 A1 9/2005 Sulamanidze et al.
2005/0251255 A1 11/2005 Metzger et al.
2005/0267321 A1 12/2005 Shadduck
2005/0267531 A1 12/2005 Ruff et al.
2005/0267532 A1 12/2005 Wu
2005/0267571 A1 12/2005 Spence et al.
2005/0268919 A1 12/2005 Conrad et al.
2005/0279365 A1 12/2005 Armijo et al.
2006/0005843 A9 1/2006 Nelson et al.
2006/0079935 A1 4/2006 Kolster
2006/0083767 A1 4/2006 Deusch et al.
2006/0093644 A1 5/2006 Quelle et al.
2006/0150986 A1 7/2006 Roue et al.
2006/0185673 A1 8/2006 Critzer et al.
2006/0206197 A1 9/2006 Morsi
2006/0207608 A1 9/2006 Hirotsuka et al.
2006/0207612 A1 9/2006 Jackson et al.
2006/0228391 A1 10/2006 Seyedin et al.
2006/0241339 A1 10/2006 Cook et al.
2006/0266369 A1 11/2006 Atkinson et al.
2006/0289015 A1 12/2006 Boucher et al.
2007/0000497 A1 1/2007 Boucher et al.
2007/0005109 A1 1/2007 Popadiuk et al.
2007/0005110 A1 1/2007 Collier et al.
2007/0102004 A1 5/2007 Nelson et al.
2007/0102010 A1 5/2007 Lemperle et al.
2007/0110788 A1 5/2007 Hissong et al.
2007/0119463 A1 5/2007 Nelson et al.
2007/0123996 A1 5/2007 Sugaya et al.
2007/0144531 A1 6/2007 Tomas et al.
2007/0144534 A1 6/2007 Mery et al.
2007/0144535 A1 6/2007 Hegde et al.
2007/0144539 A1 6/2007 Dineen et al.
2007/0190108 A1 8/2007 Datta et al.
2007/0204866 A1 9/2007 Conrad et al.
2007/0209665 A1 9/2007 Gillis et al.
2007/0227545 A1 10/2007 Conrad et al.
2007/0233276 A1 10/2007 Conrad et al.
2007/0246052 A1 10/2007 Hegde et al.
2007/0256693 A1 11/2007 Paraschac et al.
2007/0257395 A1 11/2007 Lindh et al.
2007/0261701 A1 11/2007 Sanders
2007/0267027 A1 11/2007 Nelson et al.
2007/0270631 A1 11/2007 Nelson et al.
2007/0272257 A1 11/2007 Nelson et al.
2007/0288057 A1 12/2007 Kuhnel
2007/0295338 A1 12/2007 Loomas et al.
2007/0295340 A1 12/2007 Buscemi
2008/0023012 A1 1/2008 Dineen et al.
2008/0035158 A1 2/2008 Pflueger et al.
2008/0035160 A1 2/2008 Woodson et al.
2008/0053461 A1 3/2008 Dineen et al.
2008/0066764 A1 3/2008 Paraschac et al.
2008/0066765 A1 3/2008 Paraschac et al.
2008/0066767 A1 3/2008 Paraschac et al.
2008/0066769 A1 3/2008 Dineen et al.
2008/0078411 A1 4/2008 Buscemi et al.
2008/0146868 A1 6/2008 Henri Robert et al.
2008/0167614 A1 7/2008 Tolkowsky et al.
2008/0199824 A1 8/2008 Hargadon
2008/0208265 A1 8/2008 Frazier et al.
2008/0221684 A1 9/2008 Nelson et al.
2008/0312688 A1 12/2008 Nawrocki et al.
2009/0025734 A1 1/2009 Doelling et al.
2009/0078411 A1 3/2009 Kenison et al.
2009/0165803 A1 7/2009 Bhat et al.
2010/0023055 A1 1/2010 Rousseau
2010/0024830 A1 2/2010 Rousseau et al.
2010/0030011 A1 2/2010 Weadock et al.
2010/0037901 A1 * 2/2010 Rousseau et al. ............. 128/848
2010/0080791 A1 4/2010 Rousseau et al.
2010/0106246 A1 4/2010 Rousseau et al.
2010/0108077 A1 * 5/2010 Lindh et al. .................. 128/848
2010/0132719 A1 6/2010 Jacobs et al.
2010/0137794 A1 6/2010 Knudson et al.

(56) References Cited

U.S. PATENT DOCUMENTS

| | | | | |
|---|---|---|---|---|
| 2010/0137905 | A1 | 6/2010 | Weadock et al. | |
| 2010/0158854 | A1 | 6/2010 | Puisais | |
| 2010/0163056 | A1 | 7/2010 | Tschopp et al. | |
| 2010/0211184 | A1 | 8/2010 | Rousseau et al. | |
| 2010/0234794 | A1 | 9/2010 | Weadock et al. | |
| 2010/0234946 | A1 | 9/2010 | Rousseau | |
| 2010/0256443 | A1 | 10/2010 | Griguol | |
| 2010/0294284 | A1 | 11/2010 | Hohenhorst et al. | |
| 2010/0319710 | A1 | 12/2010 | Sharkawy et al. | |
| 2011/0054522 | A1 | 3/2011 | Lindh et al. | |
| 2011/0100376 | A1 | 5/2011 | Rousseau | |
| 2011/0100377 | A1 | 5/2011 | Weadock et al. | |
| 2011/0100378 | A1 | 5/2011 | Rousseau | |
| 2011/0144558 | A1 | 6/2011 | Rousseau | |
| 2011/0174315 | A1 | 7/2011 | Zhang et al. | |
| 2011/0178439 | A1 | 7/2011 | Irwin et al. | |
| 2011/0238111 | A1 | 9/2011 | Frank | |
| 2011/0245850 | A1 | 10/2011 | Cheng et al. | |
| 2011/0282386 | A1 | 11/2011 | Friedrich | |
| 2012/0123449 | A1 | 5/2012 | Schaller et al. | |
| 2012/0160249 | A1 | 6/2012 | Garrett | |
| 2012/0245629 | A1 | 9/2012 | Gross et al. | |
| 2013/0074849 | A1 | 3/2013 | Rousseau et al. | |
| 2013/0098371 | A1 | 4/2013 | Rousseau et al. | |
| 2013/0103078 | A1* | 4/2013 | Longo et al. | 606/228 |
| 2013/0118505 | A1 | 5/2013 | Rousseau et al. | |
| 2013/0133669 | A1 | 5/2013 | Rousseau | |
| 2013/0150872 | A1 | 6/2013 | Rousseau | |
| 2013/0174857 | A1 | 7/2013 | Rousseau et al. | |
| 2013/0186412 | A1 | 7/2013 | Weadock et al. | |
| 2013/0319427 | A1 | 12/2013 | Sung et al. | |

FOREIGN PATENT DOCUMENTS

| | | | |
|---|---|---|---|
| CN | 102198010 | | 9/2011 |
| CN | 102271624 | A | 12/2011 |
| DE | 10245076 | | 4/2004 |
| EP | 2145587 | | 1/2010 |
| EP | 2386252 | A1 | 11/2011 |
| EP | 2517633 | | 10/2012 |
| FR | 2651113 | | 3/1991 |
| JP | 11-514266 | | 12/1999 |
| JP | 2001-145646 | | 5/2001 |
| JP | 2003265621 | | 9/2003 |
| JP | 2006-508708 | | 3/2006 |
| JP | 2006-517115 | | 7/2006 |
| JP | 2007-512090 | | 5/2007 |
| JP | 2007-313337 | | 12/2007 |
| JP | 2008-526286 | | 7/2008 |
| JP | 2008-529608 | | 8/2008 |
| JP | 2009-006090 | A | 1/2009 |
| JP | 2011-530385 | | 12/2011 |
| RU | 2005447 | | 1/1994 |
| RU | 2202313 | | 4/2003 |
| SU | 927236 | | 5/1982 |
| SU | 1697792 | | 12/1991 |
| WO | WO 97/13465 | | 4/1997 |
| WO | WO 99/00058 | | 1/1999 |
| WO | WO 00/66050 | | 11/2000 |
| WO | WO 01/21107 | | 3/2001 |
| WO | WO 03/096928 | | 11/2003 |
| WO | WO 2004/016196 | | 2/2004 |
| WO | WO 2004/020492 | | 3/2004 |
| WO | WO 2004/021869 | | 3/2004 |
| WO | WO 2004/021870 | | 3/2004 |
| WO | WO 2004/060311 | | 7/2004 |
| WO | WO 2004/084709 | | 10/2004 |
| WO | WO 2004/103196 | | 12/2004 |
| WO | WO 2005/046554 | | 5/2005 |
| WO | WO 2005/051292 | | 6/2005 |
| WO | WO 2005/082452 | | 9/2005 |
| WO | WO 2005/122954 | | 12/2005 |
| WO | WO 2006/012188 | | 2/2006 |
| WO | WO 2006/072571 | | 7/2006 |
| WO | WO 2006/108145 | | 10/2006 |
| WO | WO 2007/056583 | | 5/2007 |
| WO | WO 2007/075394 | | 7/2007 |
| WO | WO 2007/132449 | | 11/2007 |
| WO | WO 2007/134005 | | 11/2007 |
| WO | WO 2007/146338 | | 12/2007 |
| WO | WO 2007/149469 | | 12/2007 |
| WO | WO 2008/042058 | | 4/2008 |
| WO | WO 2008/063218 | | 5/2008 |
| WO | WO 2008/118913 | | 10/2008 |
| WO | WO 2009/023256 | | 2/2009 |
| WO | WO 2009/036094 | | 3/2009 |
| WO | WO 2010/019376 | | 2/2010 |
| WO | WO 2010/035303 | | 4/2010 |
| WO | WO 2010/051195 | | 5/2010 |
| WO | WO 2010/065341 | | 6/2010 |
| WO | WO 2012/004758 | | 1/2012 |
| WO | WO 2012/041205 | | 4/2012 |
| WO | WO 2012/064902 | | 5/2012 |
| WO | WO 2012/170468 | | 12/2012 |

OTHER PUBLICATIONS

Copy of Notification of Transmittal of the International Search Report and the Written Opinion of the International Search Authority or the Declaration mailed on Feb. 3, 2010; PCT/US2009/051921; International Filing Date: Jul. 28, 2009.

Copy of Notification of Transmittal of the International Search Report and the Written Opinion of the International Search Authority or the Declaration mailed on Dec. 25, 2010; PCT/US2010/023152; International Filing Date: Apr. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

International Search Report dated Dec. 29, 2009 for International Patent Application No. PCT/US2009/061455.

International Search Report dated Jan. 21, 2010 for International Patent Application No. PCT/US2009/052110.

International Search Report dated Apr. 29, 2010 for International Patent Application No. PCT/US2009/065293.

International Search Report dated May 25, 2010 for International Patent Application No. PCT/US2010/023152.

International Search Report dated May 25, 2010 for International Patent Application No. PCT/US2010/025778.

International Search Report dated Jan. 14, 2011 for International Patent Application No. PCT/US2010/052628.

International Search Report dated Jan. 20, 2011 for International Patent Application No. PCT/US2010/052644.

International Search Report dated Jan. 24, 2011 for International Patent Application No. PCT/US2010/052649.

International Search Report dated Feb. 28, 2011 for International Patent Application No. PCT/US2010/059673.

International Search Report dated Apr. 9, 2013 for International Patent Application No. PCT/US2012/061569.

International Search Report dated Apr. 2, 2013 for International Patent Application No. PCT/US2012/067708.

International Search Report dated Oct. 2, 2013 re: PCT/US2013/043238.

Written Opinion dated Nov. 27, 2012 for International Patent Application No. PCT/US2012/056577.

Database WPI Week 198312, Thomson Scientific, London, GB; AN 1983-D9513K XP002693421, -& SU 927 236 A1 (Petrozazodsk Univ) May 15, 1982 abstract (see figures 7 & 8).

Friedman et al., "A System and Method for Inserting a Medical Device for Treatment of Sleep Apnea via the Nasal Passage, and Device Therefor", Dec. 29, 2008, U.S. Appl. No. 61/203,758, p. 8 & p. 6/8.

MacMillan Dictionary, Fiber, MacMillan Publisher, Liminted 2009-2014.

International Search Report re: PCT/US2012/0565677 dated Nov. 27, 2012.

(56) References Cited

OTHER PUBLICATIONS

International Search Report dated May 24, 2013 for International Patent Application No. PCT/US2012/066011.
Cole et al., "Snoring: A Review and a Reassessment", J. of Otolaryngology, vol. 24, No. 5 pp. 303-306 (1995).
Harries et al., "The Surgical treatment of snoring", J. of Laryngology and Otology, vol. 110, Issue 12 pp. 1105-1106 (1996).
Huang et al., "Biomechanics of snoring", Endeavour, vol. 19(3): pp. 96100 (1995).
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
Pang, Kenny et al., "Tongue Suspension Suture in Obstructive Sleep Apnea", Operative Techniques in Otolaryngology, vol. 17, No. 4, pp. 252256 (2006).
Repose Genioglossus Advancement, INFLUENT Medical, www.influent.com, 1 page (2008).
Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).
Schwab et al., "Upper airway and soft tissue changes induced by CPAP in normal subject", Am. J. Respit. Crit. Care Med., vol. 154, No. 4 pp. 1106-1116 (1996).
Schwartz et al., "Effects of electrical stimulation to the soft palate on snoring and obstructive sleep apnea", J. Prosthetic Dentistry, vol. 76 pp. 273-281 (1996).
Shamsuzzaman et al., "Obstructive Sleep Apnea; Implications for Cardiac and Vascular Disease", JAMA vol. 290, No. 14 pp. 1906-1914 (2003).
Teles et al., "Use of Palatal Lift Prosthesis on Patient Submitted to Maxillectomy: A Case Report", Applied Cancer Res. vol. 25(3), pp. 151-154 (2005).
The Advance System, Aspire Medical, Inc. www.aspiremedical.com, 3 pp (2008).
The Pillar Procedure, Restore Medical, Inc. www.restoremedical.com, 2 pp (2008).
Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).
Wassmuth et al., "Cautery-assisted palatal stiffening operation for the treatment of obstructive sleep apnea syndrome", Otolaryngology—Head and Neck Surgery, vol. 123, pp. 55-60 (2000).
Wiltfang et al., "First results on daytime submandibular electrostimulation of suprahyoidal muscles to prevent night-time hypopharyngeal collapse in obstructive sleep apnea syndrome", Intl J. of Oral & Maxillofacial Surgery vol. 28 pp. 21-25 (1999).

* cited by examiner

SYSTEMS AND METHODS TO TREAT UPPER PHARYNGEAL AIRWAY OF OBSTRUCTIVE SLEEP APNEA PATIENTS

BACKGROUND OF THE INVENTION

1. Field of the Invention

This invention generally relates to systems and methods to treat obstructive sleep apnea (OSA), more particularly to minimally invasive solutions to prevent collapse of the upper pharyngeal airway.

2. Related Art

OSA is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

One non-surgical method available to treat OSA, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have challenges. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may be a cause of continuing irritation to the patient. Furthermore, the above procedures are not reversible in the event of adverse side effects.

Another implant system, sold under the trademark REPOSE™ by InfluENT of Concord, N.H., uses a titanium screw that is inserted into the posterior aspect of the mandible at the floor of the mouth. The screw acts as an anchor. A loop of suture is passed through the tongue base and attached to the mandibular bone screw. The REPOSE™ procedure achieves a suspension or hammock of the tongue base making it less likely for the base of the tongue to prolapse into the patient's airway during sleep. Due to the high activity of the tongue during wakefulness, however, the suture component of this device may act as a cutting element within the tongue, causing device trans-location and ultimately a loss of efficacy of the procedure thereby requiring subsequent removal.

An additional tongue suspension device developed by ASPIRE Medical is named the ADVANCE System. It is similar to the REPOSE suture suspension system for the tongue base in that it utilizes a bone screw in the mandible as an anchor, but has the advantage of being adjustable. The device further utilizes a flexible shape memory soft tissue anchor within the tongue that is shaped similar to a grappling hook, to engage the tissue within the tongue base. The soft tissue anchor is placed through a small incision in the sub-mental region of the patient's head and the suture is attached to a spool-like component attached to the mandible. Two to four weeks after healing, a small incision is made under the chin and a screw is turned to tighten the suture, thus pulling the device forward. While the device provides a simplified installation technique from within the sterile space, the anchors may suffer from device fracture and failure due to loading within the tongue musculature.

A further system is disclosed in US 2008/0208265, Frazier, et al., entitled "System and Method for Percutaneous Palate Remodeling." This publication discloses a looped tether element with one or more regions of an expanded diameter to reduce the risk of cutting through the tongue. This region is created to provide a flexible implant with a fixed expanded region, a balloon region or an in-situ expanding region. This method provides a large bearing surface on limited regions of the fiber. Additionally, this method requires a supplemental element to create the expanded region on the fiber. It is anticipated that this type of device will also be difficult to extract from tongue tissues after healing has occurred since the portion buried on the tongue base is larger in cross section than the tracks remaining from the trailing ends of the looped tether.

In spite of the above advances in OSA treatment, there remains a need for devices, systems and methods for treating OSA through minimally invasive approaches that will improve long term results with improved patient compliance and minimized patient discomfort.

SUMMARY OF THE INVENTION

Figure 1:
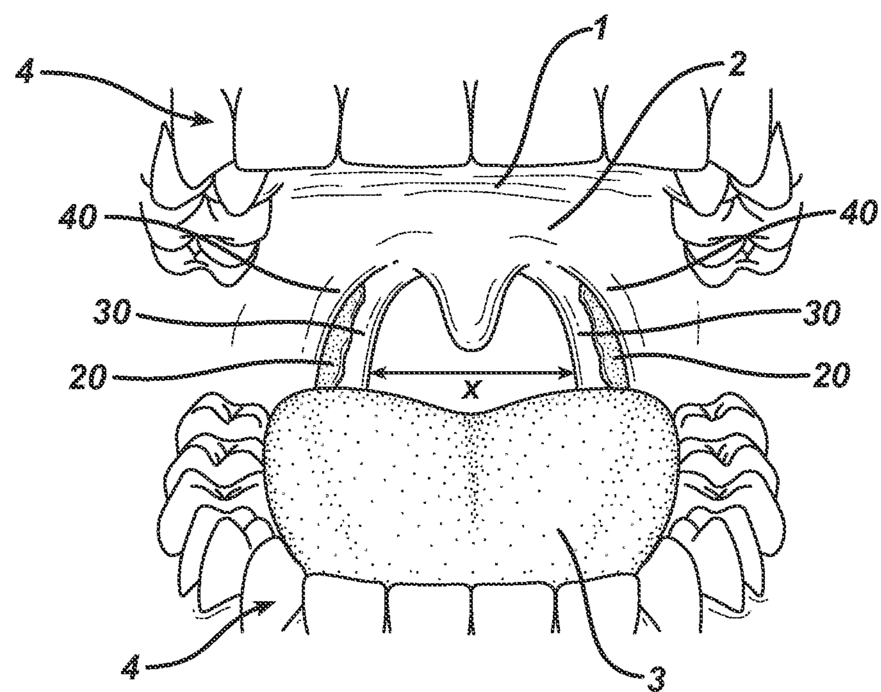
FIG. 1 depicts a frontal view of tissues in the oral cavity and oropharynx prior to the tensioning of a device to enlarge the airway.

One aspect of this invention relates to a method of supporting or reshaping a targeted tissue with a device, wherein the device comprises a central load bearing section having a first end and a second end, a first filament section having a first free end and a second end connected to the first end of the load bearing section, and a second filament section having a first free end and a second end connected to the second end of the load bearing section comprising the steps of:

a) passing the free end of the first filament section in a first direction leaving the load bearing section around the targeted tissue and into a first supporting tissue;
b) passing the free end of the second filament section into tissue in a different direction from the first direction and into a second supporting tissue while maintaining the load bearing section around the targeted tissue; and
c) applying tension to the free ends of the first and second filament sections to sufficiently support or reshape the targeted tissue.

In a preferred embodiment the first supporting tissue structure is the palatoglossal muscle, the second supporting tissue structure is the upper portion of the palatopharyngeal, and the tissue structure being supported or reshaped is the lower portion of the palatopharyngeus muscle (also referred to as the posterior pillar). In certain further embodiments neighboring muscular structures to the palatoglossal muscle and the palatopharyngeal muscle may be used as further supporting structures. One such additional muscle is the pharyngeal constrictor muscle.

Another aspect of this invention generally relates to a method of increasing the patency of an airway of a patient comprising the step of retracting or supporting one or both of the palatopharyngeal muscles.

Other embodiments of this invention relate to tissue support devices comprising:

a) a central load bearing section having a first end and a second end;
b) a first filament section having a first end and a second end with the first end connected to the first end of the load bearing section;
c) a second filament section having a first end and a second end with the first end connected to the second end of the load bearing section; and wherein the first filament section comprises barbs.

Alternate embodiments of the foregoing are hereinafter disclosed including kits and systems that incorporate the various components needed to perform the methods of this invention.

DETAILED DESCRIPTION OF PREFERRED EMBODIMENTS OF THE INVENTION

This invention discloses systems and methods using a device to retract, support or reshape soft tissue. Preferably, the device has barbed sections to hold the device in supporting tissue in a desired location and it is used to enlarge the air pathway in the oropharynx of a patient. More specifically, this invention relates to methods of increasing the patency of an airway of a patient comprising the step of retracting or supporting one or both of the palatopharyngeal muscles.

In treating the conditions of obstructive sleep apnea (and snoring due to partially obstructed airways), it is useful to understand the basic anatomy of the airway being treated and such discussion is hereinafter provided.

FIG. 1 depicts some of the major features and the boundaries of the oral cavity and the oropharnyx.

For purposes of this invention, the oral cavity proper is bounded: superiorly by the hard palate 1 and soft palate 2; inferiorly by the tongue 3 and the floor of the mouth; antero-laterally by the upper and lower teeth 4; and posteriorly by the palatoglossal arch 40.

As used herein, the palatoglossal arch is intended to describe the mucosal membrane folds that enclose the palatoglossal muscles. The palatoglossal arch is on either side of the oropharynx (and actually divides the oral cavity from the oropharynx) and is anterior to the palatopharyngeal arch. The palatopharyngeal arch is intended to describe the mucosal membrane folds that enclose the palatopharyngeal muscles on either side of the oropharynx.

The oropharynx or upper pharyngeal area as used herein is meant to describe the location of the anatomy bounded: superiorly by the soft palate 2; inferiorly by the upper border of the epiglottis and root of the tongue 3 and located posterior to the palatoglossal arch 40; and by posterior and lateral walls formed by the superior pharyngeal constrictor muscles 50 (see FIGS. 5 and 6) and middle pharyngeal constrictor muscles. Referring again to FIG. 1, the oropharynx contains tonsils 20 and the palatopharyngeal arch 30.

In preferred embodiments according to this invention, tissue in the oropharynx is targeted for retraction, support or reshaping to increase the patency of the airway.

Figure 2:
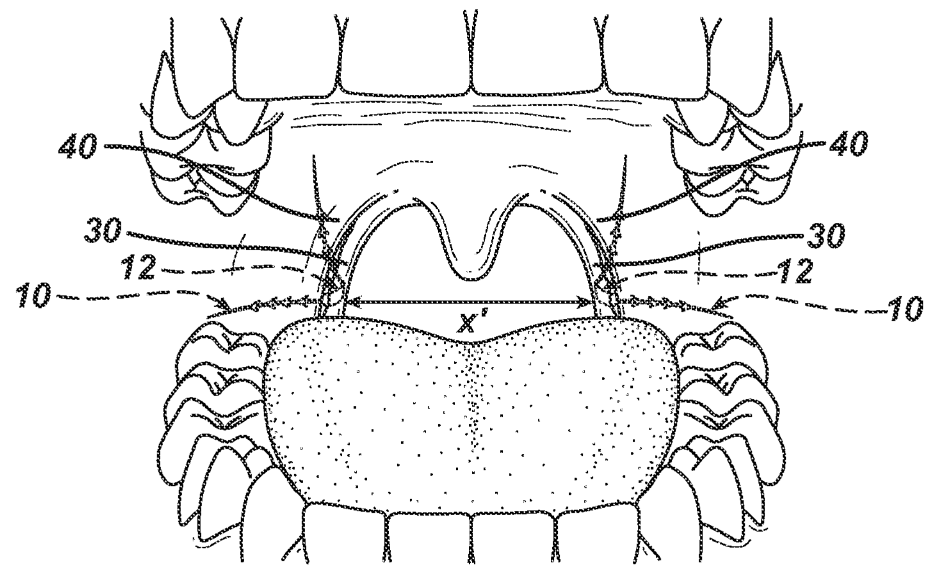
FIG. 2 shows a frontal view of tissues in the oropharynx after the tensioning of a device that enlarges the airway.

FIG. 2 shows a preferred embodiment where soft tissue in the oropharynx is retracted to increase the patency of the airway. Generally, device 10, preferably barbed, is placed in a specific location to achieve multi-vector retraction of tissue within the oropharynx. In this instance, device 10 contains a load bearing section 12 which is placed submucosally around the palatopharyngeal muscles 30. This placement of device 10 avoids "strangulation" of the tissue and a generally follows a helical path around palatopharyngeal muscle 30. The ends of device 10 are then pulled to retract, support, and/or reshape the palatopharyngeal arch. Desirably, placement and tension of the ends of the device provide multi-vector displacement of the palatopharyngeal arch which includes 1) midline to lateral; 2) dorsal to ventral; and 3) inferior to superior retraction. This retraction of tissue results in multidirectional expansion in the following vectors: 1) lateral-to-lateral; 2) posterior to anterior (i.e., from the arch toward mandible); and 3) inferior-to-superior (i.e., from palatine arch to the hard palate/upper maxilla), thus enlarging the airway. When comparing FIG. 1 to FIG. 2, one notices airway enlargement as illustrated by the lateral-lateral expansion X' in FIG. 2 being increased when compared to the lateral pretreatment distance X of FIG. 1.

Figure 3:
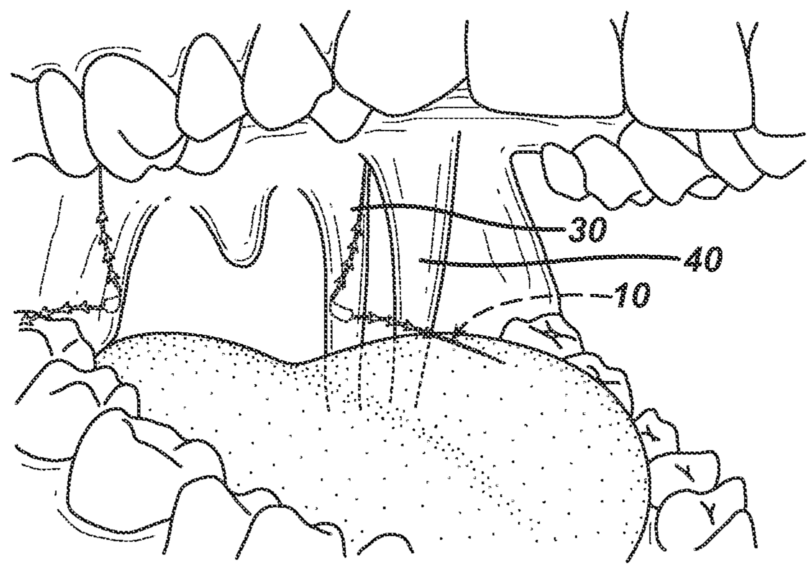
FIG. 3 is an oblique view of FIG. 1.
Figure 4:
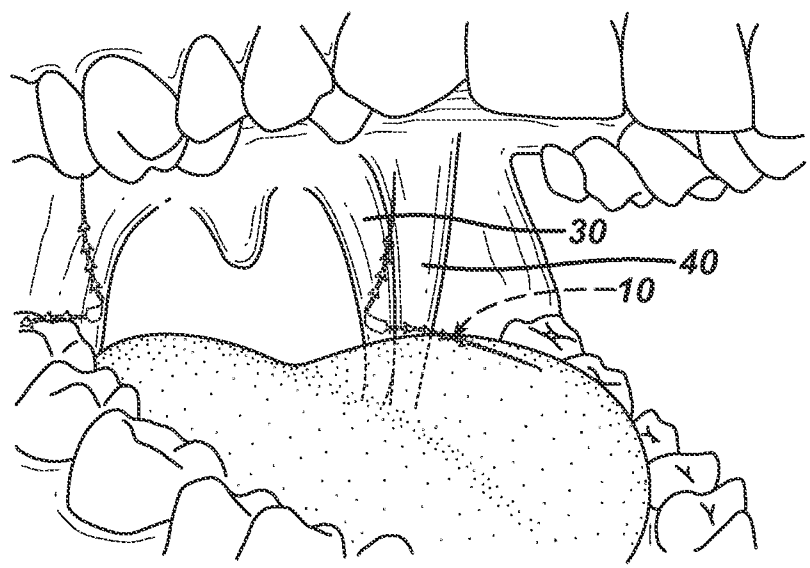
FIG. 4 is an oblique view of FIG. 2.

FIGS. 3 and 4 provide oblique views of FIGS. 1 and 2, respectively. In particular, FIG. 3 shows implantation of device 10 around palatopharyngeal muscle 30 prior to tensioning of device 10. FIG. 4 depicts palatopharyngeal muscles 30 after tensioning of device 10 wherein palatopharyngeal muscles 30 are displaced forward toward, upward and adjacent to palatoglossal muscles 40. Note that in these figures, tonsil 20 has been previously removed.

Figure 5:
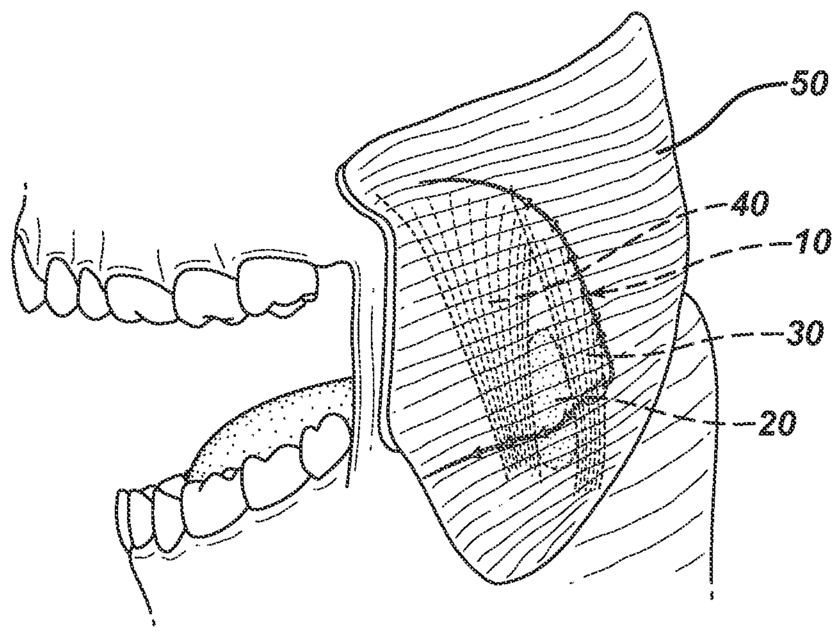
FIG. 5 is a posterior-lateral view of FIG. 1.
Figure 6:
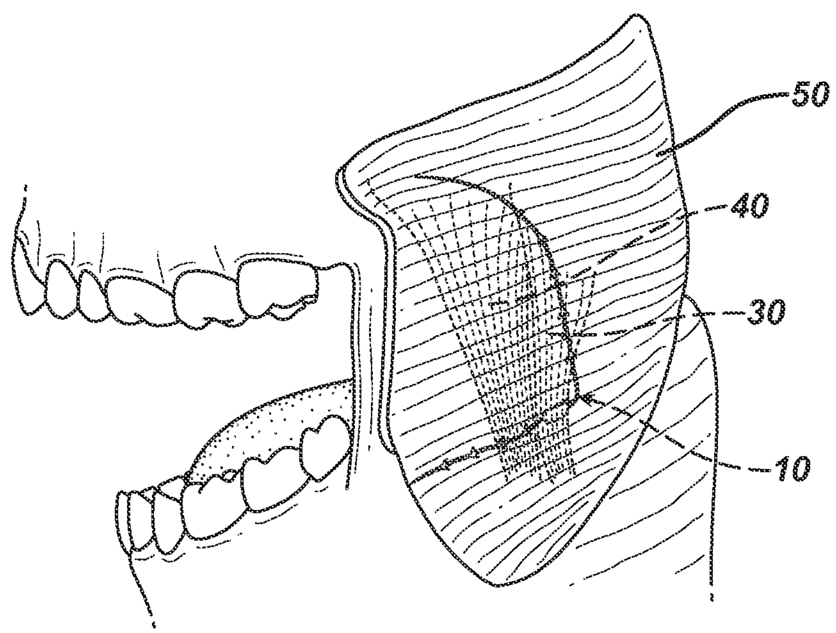
FIG. 6 is a posterior-lateral view of FIG. 2.

FIGS. 5 and 6 show posterior-lateral views of FIGS. 1 and 2, respectively with the addition of pharyngeal constrictor muscle 50. In particular, FIG. 5 shows implantation of device 10 around palatopharyngeal muscles 30 prior to tensioning of device 10 with tonsil 20 in place. FIG. 6 depicts palatopharyngeal arch 30 after tensioning of device 10 and removal of tonsil 20 wherein palatopharyngeal muscles 30 is displaced forward toward, upward and adjacent to palatoglossal muscles 40. FIGS. 5 and 6 also show the anchoring of device 10 in pharyngeal constrictor muscle 50.

FIGS. *7a-c* describe various embodiments of device 10. In particular, FIG. *7a* shows device 10 with load supporting member 12 and barbs 14 on both sides of member 12 with filaments 18 ending at tapered tips 16. Desirably, the barbs are fashioned to be bidirectional as shown in FIG. *7a*. FIG. *7b* shows an alternate embodiment with only one of the filaments 18 of device 10 having barbs 14. Finally, FIG. *7c* shows device 10 with support member 12 but with filaments 18 containing no barbs. The embodiments of FIG. *7b* and FIG.

7*c* which have barbless sections would be useful in situations where another anchoring location or anchoring means are used rather than using barbed filaments for anchoring in tissue. Thus, this invention contemplates devices 10 that may comprise barbs on both filaments, on one filament or on no filaments of the device.

Figure 8A:
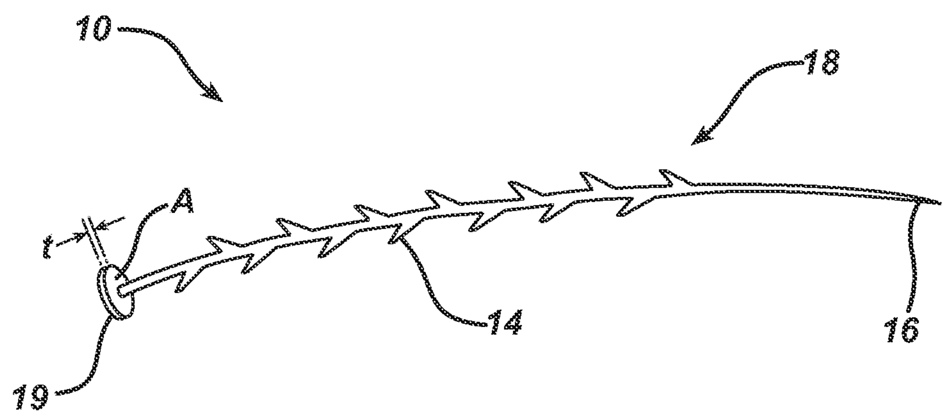
FIGS. 8*a* and 8*b* depict alternate devices useful in this invention.
Figure 8B:
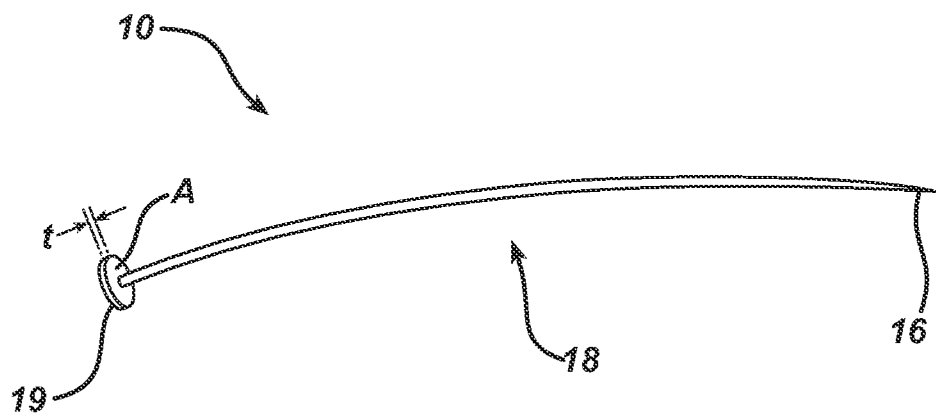

FIGS. 8*a* and 8*b* provide alternate designs for device 10 when the intermediate supporting structure 12 is not desired or needed. Referring to these figures, device 10 comprises filament 18 which may be barbed (element 14 in FIG. 8*a*) or not barbed (as depicted in FIG. 8*b*). The distal tapered tips 16 are the same as described above. The proximal tab 19 has a tissue facing surface "A" and a thickness "t" and is designed as a low profile stop which prevents device 10 from passing completely through the tissue targeted to be treated. Desirably, the low profile tab thickness ranges from 0.005 to 0.050 inches and wherein the ratio of tissue facing surface area to thickness ranges from 0.01 to 5. While tab 19 is depicted as a circular element, tab 19 may be of a variety of shapes that function to stop device 10 from completely passing through the tissue targeted to be treated and which is conformable with the targeted tissue (i.e., tab 19 has a low profile so as not to project and interfere with tissue adjacent to the targeted tissue and which achieves the goal of the treatment such as increased airway patency of the oropharynx). Examples of additional suitable shapes for tab 19 include but are not limited to flat, planar shapes and elliptical shapes.

Device 10 of FIGS. 8*a* and 8*b* are most useful when only a targeted retraction of tissue is desired. For example, device may be passed through the desired tissue with tissue retraction being concentrated where the tab interfaces with the tissue that has been targeted to be treated. While not forming any device claims to this invention, alternative devices useful with the methods of this invention are found in US2005/0267531. This publication provides alternative barbed filament devices that include various tab or "anchor" designs that may also anchor in tissue such as depicted in FIGS. 39 A and 39 B in contrast to the devices 10 depicted in FIGS. 8*a* and 8*b* of this invention.

Ends 16 of device 10 may also have attached to it one or more needles. Preferably, the needle tips are tapered and end in a point. Additionally a needle attached to one end of the device need not be the same size as a needle attached to the other end of the device. The selection of size and type of needle would be determined by one of skill of the art and designed for the requirements of the specific application the device is being used for.

The distinct sections of device 10 are designed for different and separate functionalities. For example, the load bearing section 12 is the center broader section that will eventually be implanted under a mucosal layer. The load bearing section 12 serves as a brace during tensioning/lifting the tissue without cutting through tissue. Preferably, both filaments 18 extending from section 12 of the device are barbed and serve to support and reposition the tissue. Preferably, the barbs 14 can collapse during insertion to reduce insertion drag as well as reduce damage to tissue. The lead ends 16 of filaments 18 are desirably clear, tapered, and without barbs. These ends are tapered to reduce the sensation in the patient's mouth during implantation. Line markers (e.g., graduations) may be placed on lead ends 16 of filaments to indicate displacement or depth of placement peri-operatively or post-operatively. The markers may be visible (e.g., colored) or radio-opaque. The load bearing section 12 may also have visible or radio-opaque markers. Load bearing section 12 may be of a variety of shapes that functions support the tissue targeted to be treated and which is conformable with the targeted tissue (i.e., has a low profile so as not to project and interfere with tissue adjacent to the targeted tissue and which achieves the goal of the treatment such as increased airway patency of the oropharynx). Examples of suitable shapes for load bearing section 12 include but are not limited to oblong, rectangular, circular and elliptical.

Barbs 14 of device 10 may be of any of a variety of designs and are intended to grasp and anchor themselves in tissue to maintain the desired position for device 10. Barbs 14 can be a series of protruding elements either molded on to the filament 18 such as disclosed in U.S. Pat. No. 4,069,865 and U.S. Pat. No. 5,123,913 or added as separate components on to filament 18 as disclosed in US2006/0079935. Barbs 14 can also be cuts created with blades along filament 18 as disclosed in U.S. Pat. No. 3,123,007 and US2007/0005109. In other instances, barbs 14 along with filament 18 can be die cut as disclosed in US 2003/0149447 and U.S. Pat. No. 7,850,894. Furthermore, the barbs on one filament may be different from the barbs on the other filament and the length of the barbed sections may be of different length. The barbs may also be asymmetrically located with respect to the load bearing section and multiple and different barb geometries may be present on one device (e.g., possibly larger with a shorter barbed section). The various embodiments of the device will depend on the desired tissue being treated and the manner in which the device will be anchored.

Device 10 may be made of many biocompatible materials. Examples of suitable materials include but are not limited to non-absorbable materials such as polyamides (e.g., polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g., polyethylene terephthalate, polybutyl terephthalate, copolymers and blends thereof), fluoropolymers (e.g., polytetrafluoroethylene and polyvinylidene fluoride) Poly (hexafluoropropylene -VDF), polyaryletherketones, polyolefins (e.g., polypropylene including isotactic and syndiotactic polypropylene and blends thereof, as well as, blends composed predominately of isotactic or syndiotactic polypropylene blended with heterotactic polypropylene and/or polyethylene (such as is described in U.S. Pat. No. 4,557,264, assigned to Ethicon, Inc., hereby incorporated by reference in its entirety)) and combinations thereof.

Additionally, bioabsorbable materials may be used in this invention either alone or in combination with the non-absorbable biocompatible material described above. In the case that a fully bioabsorbable material is used, the application that this material is used would most likely be one in which a temporary retraction or support of tissue is desired and that once the absorbable material is absorbed, the supported tissue would return to its natural tone. Suitable bioabsorbable materials for use in this invention include, but are not limited to, aliphatic polyesters which include but are not limited to homopolymers and copolymers of lactide (which includes lactic acid, d-,l- and meso lactide), glycolide (including glycolic acid), ϵ-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ϵ-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Combinations of absorbable and non-absorbable materials may also be utilized to produce a device with tailored properties and configurations. One such configuration contemplated is one which provides devices with absorbable coverings obtained through processing such as by coating and/or co-extrusion.

The selection of the materials for use in the device would be determined by one of the skill of the art and designed for the requirements of the specific application. The most preferred materials are non-absorbable for at least one component for long term efficacy in enabling the supported tissue to remain in the orientation achieved during implantation. Thus of the foregoing materials, the preferred device materials are polyesters (e.g. polyethylene terephthalate, polybutyl terephthalate, copolymers and blends thereof), fluoropolymers (e.g. polytetrafluoroethylene and polyvinylidene fluoride) Poly (hexafluoropropylene -VDF), polyaryletherketones, polyolefins (e.g. polypropylene including isotactic and syndiotactic polypropylene). The most preferred materials are poly (hexafluoropropylene -VDF) and polypropylene.

Figure 7A:
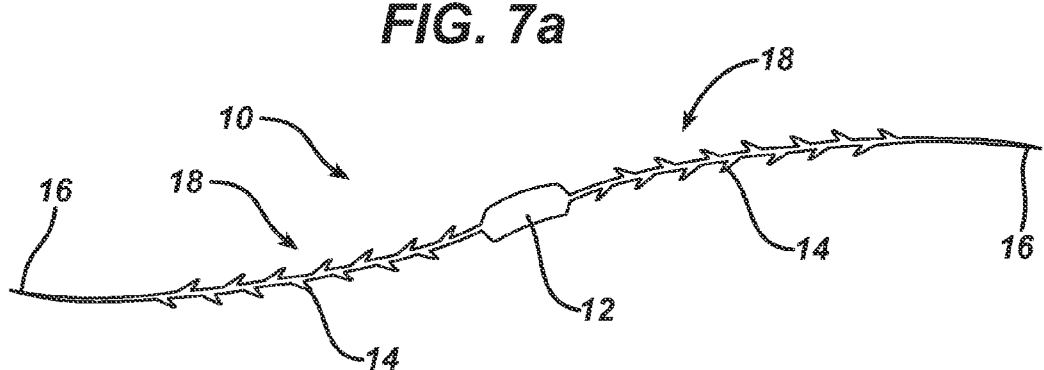
FIGS. 7*a-c* depict various forms of a device useful in this invention.
Figure 7B:
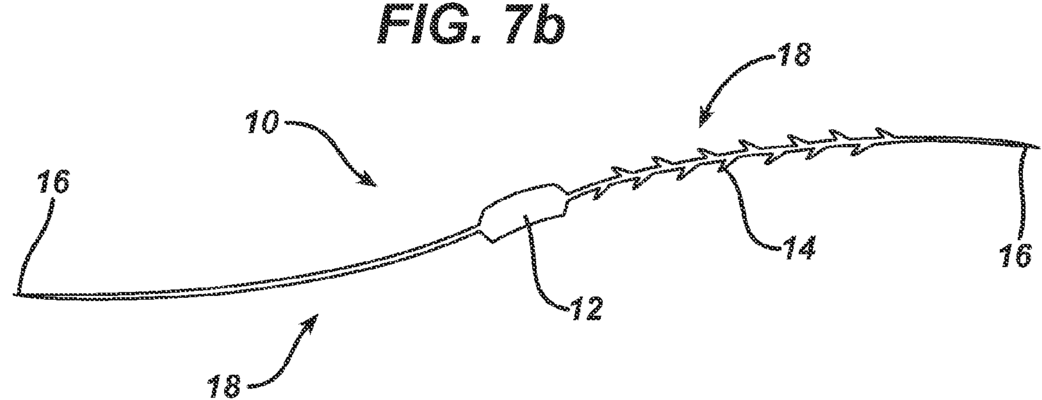
Figure 7C:
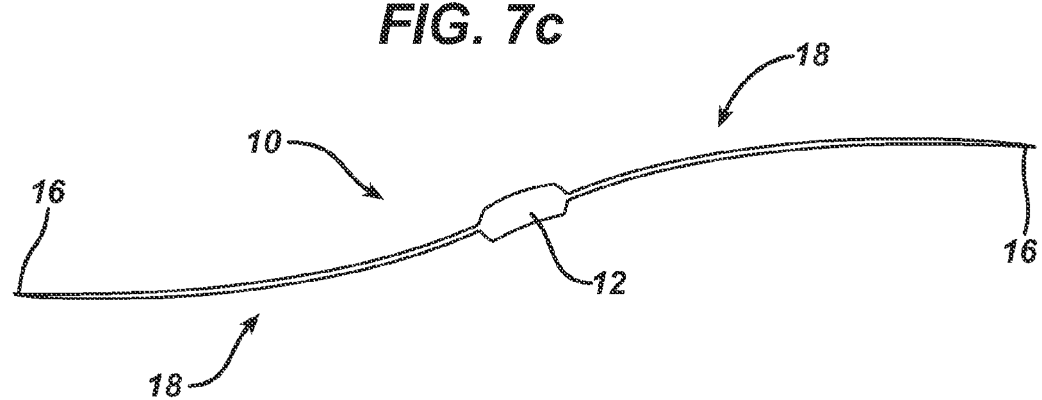

To achieve increased patency of the airway described in the forgoing discussion, two methods of delivery of the device are contemplated. The first described method is for using a bidirectional device such as depicted in FIGS. 7*a*-7*c*, i.e., for those devices which have a load bearing or support portion. The second method described may be used for the bidirectional devices of FIGS. 7*a*-7*c*, i.e., for those devices which have a load bearing or support portion and for the case of unidirectional devices such as depicted in FIGS. 8*a* and 8*b* or described in US2005/0267531 devices. For either method, the tonsils may or may not be present. Most preferably, however, removal of the tonsils is desirable as this will provide more room for retraction, for example, of the palatopharyngeal arch.

The first method for the delivery of the support device is through the use of needles. The technique generally involves inserting the device with a needle attached to one or both ends of the device from the back of the mouth and into the oropharynx area and driving the needle(s) forward following the pathway of the method described below. One important feature for these needles is to have a curvature and chord depth that enables passage through tissue at a depth of about 2 mm to less than about 2 cm and having an entry and exit points between about 0.5 and 3 inches to avoid deep penetration during placement, thus minimizing the potential of damaging critical structures like the internal carotid artery. Additionally use of short needles may be desired to create an undulating path that would result with the load of supporting the targeted tissue being distributed along a path of multiple force vectors.

More specifically the method comprises the steps of:

a) removing the tonsils, if needed, if not, creating an incision through the mucosal layer at the medial aspect of the palatopharyngeal fold;

b) inserting a first needle attached to the first end of the device having a central load bearing section and a first filament end and a second filament end extending from either end of the central load bearing section around or into the medial aspect of the palatopharyngeal muscle within the incision;

c) passing the first needle at the first entry point through the palatoglossal muscle and directing the needle between the mucosa and pharyngeal constrictor muscle or within the pharyngeal constrictor muscle caudal to the last molar and exit at the first exit point;

d) inserting a second needle into the medial aspect of the palatopharyngeal muscle within the incision slightly lateral and superior to the insertion point of the first needle at a second entry point;

e) passing the second needle around or through the palatopharyngeal muscle and directing the needle through tissue between the palatopharyngeal and superior pharyngeal constrictor muscles or within palatopharyngeal muscle toward the hard palate and exit at the second exit point;

f) pulling both ends of the device that are attached to the first needle and second needle until the center load support section is nesting at the apex of the palatopharyngeal muscle;

g) pulling the filament ends of the device at the same time or individually to adjust the tension/displacement of the palatopharyngeal muscle to increase the patency of the airway; and h) trimming the excess of the filament ends of the device or allowing the ends to remain under the mucosa.

The above method desirably is repeated for treatment of the palatopharyngeal arch on the opposite side of the oropharynx.

The extent that the airway patency is improved may be determined by taking the following measurements and comparing these measurements to measurements taken prior to treatment:

i) Lateral—lateral aspect: Distance between the palatopharyngeal arches;

ii) Vertical opening (anterior-posterior): Distance between the uvula (or palatopharyngeal arches) and posterior pharyngeal wall; and iii) Distance from the tip of uvula (or palatopharyngeal arches) to the hard palate.

The second method is to use commonly available instruments such as a suture passer or a trocar system with a tube with a snare, going in from the front of the mouth following the pathway described in the first method above and pulling the device 10 through. The suture passer or trocar will however travels in a reverse direction of device 10 as described in the first method above.

Therefore entry of the trocar or suture passer is made from the exit points previous described and exit from the entry points previously described. The suture passer has a grasping end to engage with filament 18 to pull it through the pathway described above. The trocar system will have the snare engaging with filament 18 to pull it through the pathway described above. The design of suture passer or trocar desirably comprises a pre-shaped wire or tube configured to the desired angle that will give user the control to deliver the tissue support device according to the pathway described above. The suture passer or trocar is preferably made of steel or nitinol.

In the case of unidirectional devices such as depicted in FIGS. 8*a* and 8*b* or described in US2005/0267531, the method of increasing the patency of an airway of a patient comprises the step of retracting or supporting one or both of the palatopharyngeal muscles wherein the step of retracting or supporting the palatopharyngeal muscle(s) comprises:

a) piercing at least one of the palatopharyngeal muscles with a device comprising a filament extending from a tab wherein the filament end of the device pierces at least one of the palatopharyngeal muscles;

b) drawing the filament end of the device through the at least one palatopharyngeal muscle until the tab rests at the point where the palatopharyngeal muscle had been pierced; and c) applying tension to the filament end of the device to retract or support the at least one of the palatopharyngeal muscles.

In preferred embodiments the filament is barbed, and desirably two devices each comprising a barbed filament and tab both pierce at least one of the palatopharyngeal muscles and the filament end of one of the devices anchors in the palatoglossal muscle and the filament end of the second of the devices anchors in the palatopharyngeal muscle.

This invention further contemplates kits or systems that provide the various components needed to perform the foregoing described methods. For example, the system or kit may comprise the device 10 in various sizes and include needles attached to the filament ends of the device in a variety of sizes and shapes. Additionally the system or kit may contain the tissue support device fitted with needles of various shapes and sizes. A suture passer, sized to deliver the tissues support design and optionally a trocar may be provided.

It should be understood that the foregoing disclosure and description of the present invention are illustrative and explanatory thereof and various changes in the size, shape and materials as well as in the description of the preferred embodiments may be made without departing from the spirit of the invention.

What is claimed is:

1. A method for supporting or reshaping a palatopharyngeal muscle with a device, wherein the device comprises a central load bearing section having a first end and a second end, a first filament section having a first free end and a second end connected to the first end of the load bearing section, and a second filament section having a first free end and a second end connected to the second end of the load bearing section comprising the steps of:

a) passing the free end of the first filament section in a first direction leaving the load bearing section around the palatopharyngeal muscle and into a first supporting tissue;

b) passing the free end of the second filament section into tissue in a different direction from the first direction and into a second supporting tissue while maintaining the load bearing section around the palatopharyngeal muscle wherein the passing of the filaments follow a helical path; and c) applying tension to the free ends of the first and second filament sections to sufficiently support or reshape the palatopharyngeal muscle to achieve multi-vector retraction.

2. The method of claim 1 wherein the first supporting tissue is the palatoglossal muscle and neighboring muscular structures and the second supporting tissue is the palatopharyngeal muscle and neighboring muscular structures including a superior pharyngeal constrictor muscle.

3. The method of claim 2 wherein the applied tension to the free ends of the filaments results in the palatopharyngeal muscle being retracted toward the palatoglossal muscle.

4. The method of claim 3 wherein the first filament section contains barbs.

5. The method of claim 4 wherein both the first and second filament sections contain barbs.

6. The method of claim 5 wherein the barbs of the first filament section are oriented in a direction opposite to an orientation of the barbs of the second filament section.

7. The method of claim 3 wherein the second filament section contains barbs.

8. A method for increasing a patency of an airway of a patient, the airway comprising palatopharyngeal muscles and palatoglossal muscles, the method comprising the step of retracting or supporting one or both of the palatopharyngeal muscles, wherein the step of retracting or supporting the palatopharyngeal muscle(s) comprises:

a) piercing at least one of the palatopharyngeal muscles at a point with a device comprising a filament extending from a tab wherein the filament pierces at least one of the palatopharyngeal muscles;

b) drawing the filament through the at least one palatopharyngeal muscle until the tab rests at the point where the palatopharyngeal muscle had been pierced wherein the drawing of the filament follows a helical path; and c) applying tension to the filament to retract or support the at least one of the palatopharyngeal muscles.

9. The method of claim 8 where the filament is barbed.

10. The method of claim 9 wherein a first device and a second device each comprising a barbed filament and tab both pierce at least one of the palatopharyngeal muscles and the filament first device anchors in the palatoglossal muscle and the filament of the second device anchors in the palatopharyngeal muscle.

* * * * *